US012597505B2

(12) United States Patent
Nakamura

(10) Patent No.: US 12,597,505 B2
(45) Date of Patent: Apr. 7, 2026

(54) DOCUMENT CREATION SUPPORT APPARATUS, DOCUMENT CREATION SUPPORT METHOD, AND DOCUMENT CREATION SUPPORT PROGRAM

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 261 days.

(21) Appl. No.: 18/481,194

(22) Filed: Oct. 4, 2023

(65) Prior Publication Data

US 2024/0029870 A1 Jan. 25, 2024

Related U.S. Application Data

(63) Continuation of application No. PCT/JP2022/014667, filed on Mar. 25, 2022.

(30) Foreign Application Priority Data

Apr. 14, 2021 (JP) ................................. 2021-068674
Dec. 22, 2021 (JP) ................................. 2021-208523

(51) Int. Cl.
| | |
|---|---|
| *G16H 30/40* | (2018.01) |
| *G06T 7/00* | (2017.01) |
| *G06T 7/11* | (2017.01) |
| *G06V 10/20* | (2022.01) |
| *G06V 10/82* | (2022.01) |
| *G16H 15/00* | (2018.01) |

(52) U.S. Cl.
CPC ........... *G16H 30/40* (2018.01); *G06T 7/0012* (2013.01); *G06T 7/11* (2017.01); *G06V 10/255* (2022.01); *G06V 10/82* (2022.01); *G16H*

*15/00* (2018.01); *G06T 2207/10072* (2013.01); *G06T 2207/20084* (2013.01); *G06V 2201/03* (2022.01)

(58) Field of Classification Search
None
See application file for complete search history.

(56) References Cited

U.S. PATENT DOCUMENTS

| | | |
|---|---|---|
| 2010/0189366 A1 | 7/2010 | Iizuka et al. |
| 2012/0176408 A1 | 7/2012 | Moriya |
| 2016/0350480 A1* | 12/2016 | Gerdeman ............. G16H 40/20 |

(Continued)

FOREIGN PATENT DOCUMENTS

| | | | | |
|---|---|---|---|---|
| EP | 3342343 B1 * | 11/2019 | ............. | A61B 5/002 |
| JP | 2009082443 | 4/2009 | | |

(Continued)

OTHER PUBLICATIONS

"International Search Report (Form PCT/ISA/210) of PCT/JP2022/014667", mailed on Jun. 14, 2022, with English translation thereof, pp. 1-5.

(Continued)

*Primary Examiner* — David Ometz
(74) *Attorney, Agent, or Firm* — JCIPRNET

(57) ABSTRACT

A document creation support apparatus comprising at least one processor, wherein the processor is configured to: extracts regions having one or more preset physical features from a medical image, and generates a comment on findings using a disease name associated with a physical feature of at least one of the extracted regions.

20 Claims, 13 Drawing Sheets

(56)           References Cited

U.S. PATENT DOCUMENTS

| | | | |
|---|---|---|---|
| 2018/0177446 | A1 | 6/2018 | Okabe et al. |
| 2019/0267132 | A1 * | 8/2019 | Fuchigami .............. G06T 11/60 |
| 2020/0043600 | A1 * | 2/2020 | Glottmann ............ G16H 15/00 |
| 2022/0028510 | A1 | 1/2022 | Nakamura et al. |

FOREIGN PATENT DOCUMENTS

| | | | |
|---|---|---|---|
| JP | 2011086276 | 4/2011 | |
| JP | 2017191457 | 10/2017 | |
| JP | 2020009186 | 1/2020 | |
| WO | WO-2009041586 A1 * | 4/2009 | ............ G16H 50/70 |
| WO | 2017033516 | 3/2017 | |
| WO | 2020129385 | 6/2020 | |
| WO | 2020209382 | 10/2020 | |

OTHER PUBLICATIONS

"Written Opinion of the International Searching Authority (Form PCT/ISA/237) of PCT/JP2022/014667", mailed on Jun. 14, 2022, with English translation thereof, pp. 1-8.
"Notice of Reasons for Refusal of Japan Counterpart Application", issued on Dec. 16, 2025, with English translation thereof, p. 1-p. 6.

* cited by examiner

~32

| ORGAN | PHYSICAL FEATURE | DISEASE NAME |
|---|---|---|
| BRAIN | WHITE MASS | CEREBRAL HEMORRHAGE |
| BRAIN | DARK MASS | CEREBRAL INFARCTION |
| LIVER | UNEVENNESS | LIVER CIRRHOSIS |
| LARGE INTESTINE | PROTRUSION | COLON POLYP |
| ... | ... | ... |

~10

DOCUMENT CREATION SUPPORT APPARATUS

~40 ACQUISITION UNIT

~42 EXTRACTION UNIT

~44 DISPLAY CONTROL UNIT

~46 RECEPTION UNIT

~48 GENERATION UNIT

EXTRACTION

- BRAIN TUMOR IS FOUND.
- CEREBRAL HEMORRHAGE IS FOUND.

FIG. 11

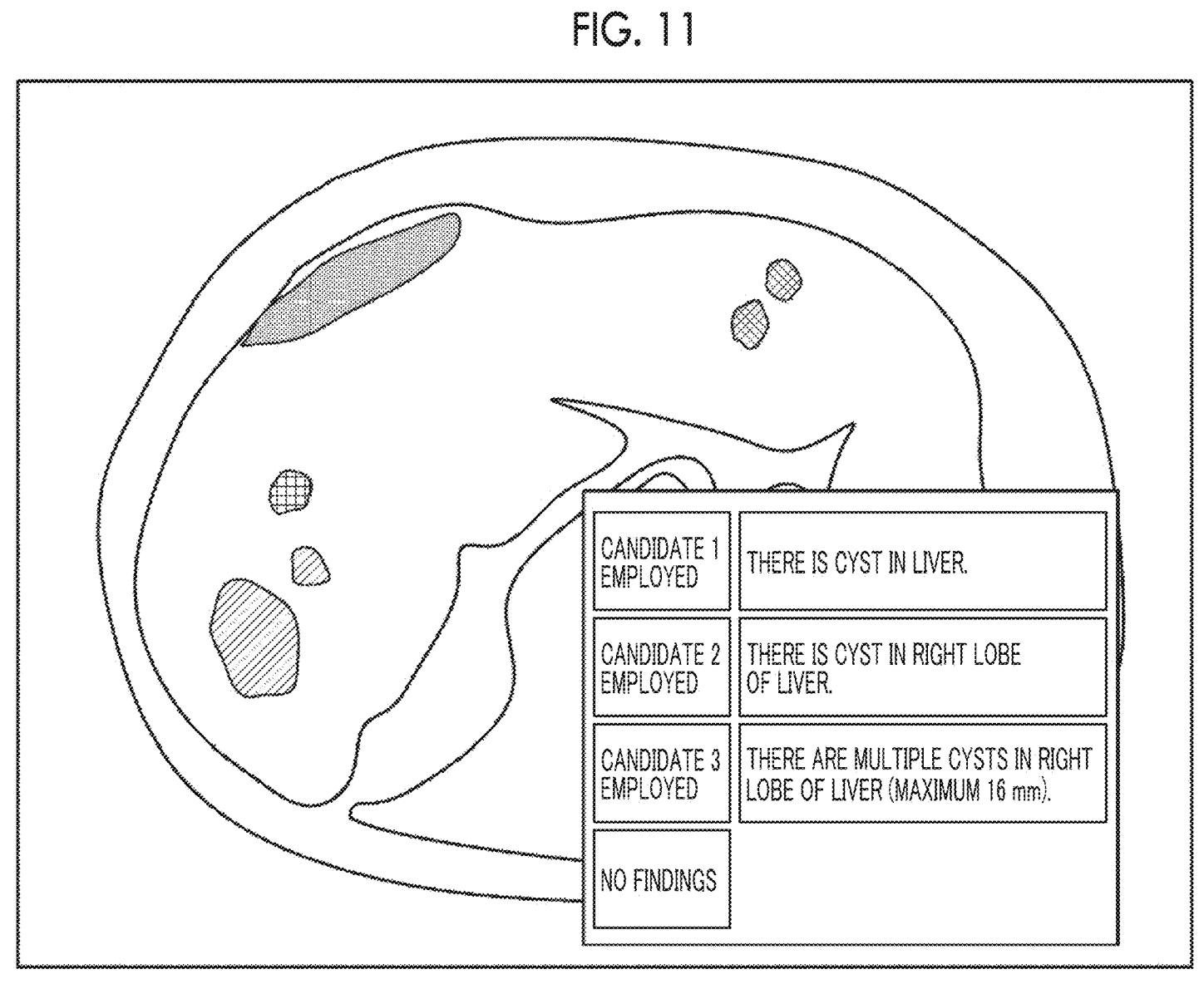

| CANDIDATE 1 EMPLOYED | THERE IS CYST IN LIVER. |
| CANDIDATE 2 EMPLOYED | THERE IS CYST IN RIGHT LOBE OF LIVER. |
| CANDIDATE 3 EMPLOYED | THERE ARE MULTIPLE CYSTS IN RIGHT LOBE OF LIVER (MAXIMUM 16 mm). |
| NO FINDINGS | |

FIG. 12

| CANDIDATE 1 EMPLOYED | THERE IS LIVER CIRRHOSIS IN LIVER. |
| CANDIDATE 2 EMPLOYED | UNEVENNESS IS FOUND ON SURFACE OF LIVER, AND LIVER CIRRHOSIS IS SUSPECTED. |
| CANDIDATE 3 EMPLOYED | SERRATED CHANGE IS FOUND IN MARGIN OF LIVER, AND LIVER CIRRHOSIS IS SUSPECTED. |
| CANDIDATE 4 EMPLOYED | ATROPHY IS FOUND IN BOTH LOBES OF LIVER, AND CHRONIC LIVER INJURY IS SUSPECTED. |
| NO FINDINGS | |

Figure 16:
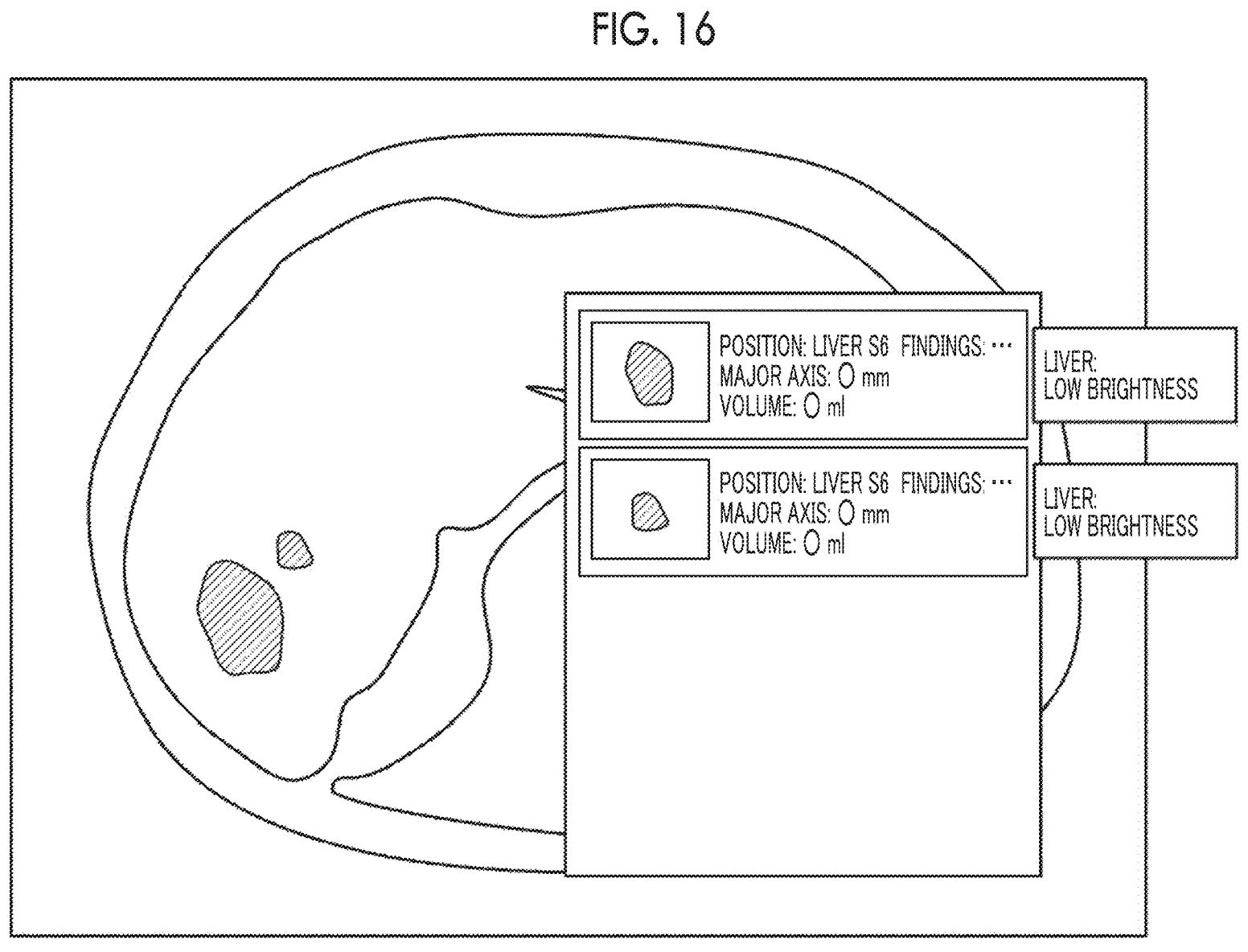

LIVER:
LOW BRIGHTNESS

LIVER:
LOW BRIGHTNESS

POSITION: LIVER S6   FINDINGS: ...
MAJOR AXIS: O mm
VOLUME: O ml

POSITION: LIVER S6   FINDINGS: ...
MAJOR AXIS: O mm
VOLUME: O ml

DOCUMENT CREATION SUPPORT APPARATUS, DOCUMENT CREATION SUPPORT METHOD, AND DOCUMENT CREATION SUPPORT PROGRAM

CROSS-REFERENCE TO RELATED APPLICATIONS

This application is a continuation of International Application No. PCT/JP2022/014667, filed on Mar. 25, 2022, which claims priority from Japanese Patent Application No. 2021-068674, filed on Apr. 14, 2021 and Japanese Patent Application No. 2021-208523, filed on Dec. 22, 2021. The entire disclosure of each of the above applications is incorporated herein by reference.

BACKGROUND

1. Technical Field

The present disclosure relates to a document creation support apparatus, a document creation support method, and a document creation support program.

2. Description of the Related Art

WO2020/209382A discloses a technology of detecting a plurality of findings representing features of an abnormal shadow included in a medical image, specifying at least one finding to be used for creating an interpretation report from among the detected findings, and creating an interpretation report using the specified finding.

SUMMARY

In the technology disclosed in WO2020/209382A, various processes are executed, such as a process of detecting an abnormal shadow from a medical image, a process of detecting a plurality of findings representing features of the abnormal shadow, and a process of specifying at least one finding to be used for generating an interpretation report from among the plurality of findings. That is, the technology disclosed in WO2020/209382A cannot easily support generation of the interpretation report.

The present disclosure has been made in view of the above circumstances, and an object of the present disclosure is to provide a document creation support apparatus, a document creation support method, and a document creation support program capable of easily supporting generation of an interpretation report.

According to an aspect of the present disclosure, there is provided a document creation support apparatus comprising at least one processor, in which the processor is configured to: extract regions having one or more preset physical features from a medical image; and generate a comment on findings using a disease name associated with a physical feature of at least one of the extracted regions.

In addition, in the document creation support apparatus according to the aspect of the present disclosure, the processor may be configured to: perform control to display information indicating the extracted region; receive information indicating a selected region from among the extracted regions; and generate the comment on findings using a disease name associated with the physical feature of the selected region.

In addition, in the document creation support apparatus according to the aspect of the present disclosure, the processor may be configured to refer to data in which the physical features and disease names are associated with each other, and generate the comment on findings using the disease name associated with the physical feature.

In addition, in the document creation support apparatus according to the aspect of the present disclosure, the processor may be configured to extract, from the medical image, a region of which a pixel value is within a set range as the region having the physical feature.

In addition, in the document creation support apparatus according to the aspect of the present disclosure, the processor may be configured to extract, from the medical image, a region of a shape having a set feature as the region having the physical feature.

In addition, in the document creation support apparatus according to the aspect of the present disclosure, the physical feature may be set for each organ.

In addition, in the document creation support apparatus according to the aspect of the present disclosure, a plurality of disease names may be associated with the physical feature.

In addition, in the document creation support apparatus according to the aspect of the present disclosure, the processor may be configured to perform control to highlight the extracted region.

In addition, in the document creation support apparatus according to the aspect of the present disclosure, the processor may be configured to perform control to display the generated comment on findings.

In addition, in the document creation support apparatus according to the aspect of the present disclosure, the processor may be configured to generate a plurality of comments on findings for one disease name.

In addition, in the document creation support apparatus according to the aspect of the present disclosure, the processor may be configured to generate a plurality of comments on findings using a plurality of disease names.

In addition, in the document creation support apparatus according to the aspect of the present disclosure, the processor may be configured to: perform control to display the plurality of generated comments on findings; and receive a comment on findings selected by a user.

In addition, in the document creation support apparatus according to the aspect of the present disclosure, the processor may be configured to: estimate a disease name using the medical image; and control a display mode of the plurality of generated comments on findings based on an estimation result.

In addition, in the document creation support apparatus according to the aspect of the present disclosure, the processor may be configured to estimate the disease name based on a degree of similarity between the medical image and an image prepared in advance for each disease.

In addition, in the document creation support apparatus according to the aspect of the present disclosure, the processor may be configured to estimate the disease name based on a statistical value of pixel values in the region extracted from the medical image.

In addition, in the document creation support apparatus according to the aspect of the present disclosure, the processor may be configured to estimate the disease name based on the medical image and a trained model that has been trained in advance using training data including a medical image for learning and a disease name of a disease included in the medical image for learning.

In addition, in the document creation support apparatus according to the aspect of the present disclosure, the processor may be configured to perform control to display, in an identifiable manner, a status for the extracted region among a plurality of statuses related to creation work of a medical document by a user.

In addition, in the document creation support apparatus according to the aspect of the present disclosure, the plurality of statuses may include two or more of a status in which the user has not confirmed the region, a status in which the user has designated the region as a target of the creation work and the creation work is incomplete, a status in which the user has designated that the region is excluded from the target of the creation work, and a status that the creation work for the region is completed.

In addition, in the document creation support apparatus according to the aspect of the present disclosure, the processor may be configured to, in a case where the status is the status in which the user has designated the region as the target of the creation work and the creation work is incomplete, perform control to display the status in an identifiable manner by adding a predetermined mark to the region.

In addition, in the document creation support apparatus according to the aspect of the present disclosure, the processor may be configured to further perform control to display a list of information regarding each of a plurality of the regions.

In addition, in the document creation support apparatus according to the aspect of the present disclosure, the processor may be configured to perform control to display the list of the information regarding each of the plurality of regions for each of the statuses.

In addition, according to another aspect of the present disclosure, there is provided a document creation support method executed by a processor provided in a document creation support apparatus, the method comprising: extracting regions having one or more preset physical features from a medical image; and generating a comment on findings using a disease name associated with a physical feature of at least one of the extracted regions.

In addition, according to another aspect of the present disclosure, there is provided a document creation support program for causing a processor provided in a document creation support apparatus to execute: extracting regions having one or more preset physical features from a medical image; and generating a comment on findings using a disease name associated with a physical feature of at least one of the extracted regions.

According to the aspects of the present disclosure, it is possible to easily support generation of an interpretation report.

BRIEF DESCRIPTION OF THE DRAWINGS

FIG. 11 is a diagram showing an example of a comment-on-findings display screen.

FIG. 12 is a diagram showing an example of a comment-on-findings display screen.

FIG. 13 is a diagram showing an example of a status display screen.

FIG. 15 is a diagram showing an example of a list display screen.

FIG. 16 is a diagram showing an example of a list display screen.

DETAILED DESCRIPTION

Hereinafter, form examples for implementing a technology of the present disclosure will be described in detail with reference to the drawings.

First Embodiment

First, a configuration of a medical information system 1 to which a document creation support apparatus according to the disclosed technology is applied will be described with reference to FIG. 1. The medical information system 1 is a system for performing imaging of a diagnosis target part of a subject and storing of a medical image acquired by the imaging based on an examination order from a doctor in a medical department using a known ordering system. In addition, the medical information system 1 is a system for performing interpretation of a medical image and creation of an interpretation report by a radiologist, and viewing the interpretation report and detailed observation of the medical image to be interpreted by a doctor of a medical department that is a request source.

Figure 1:
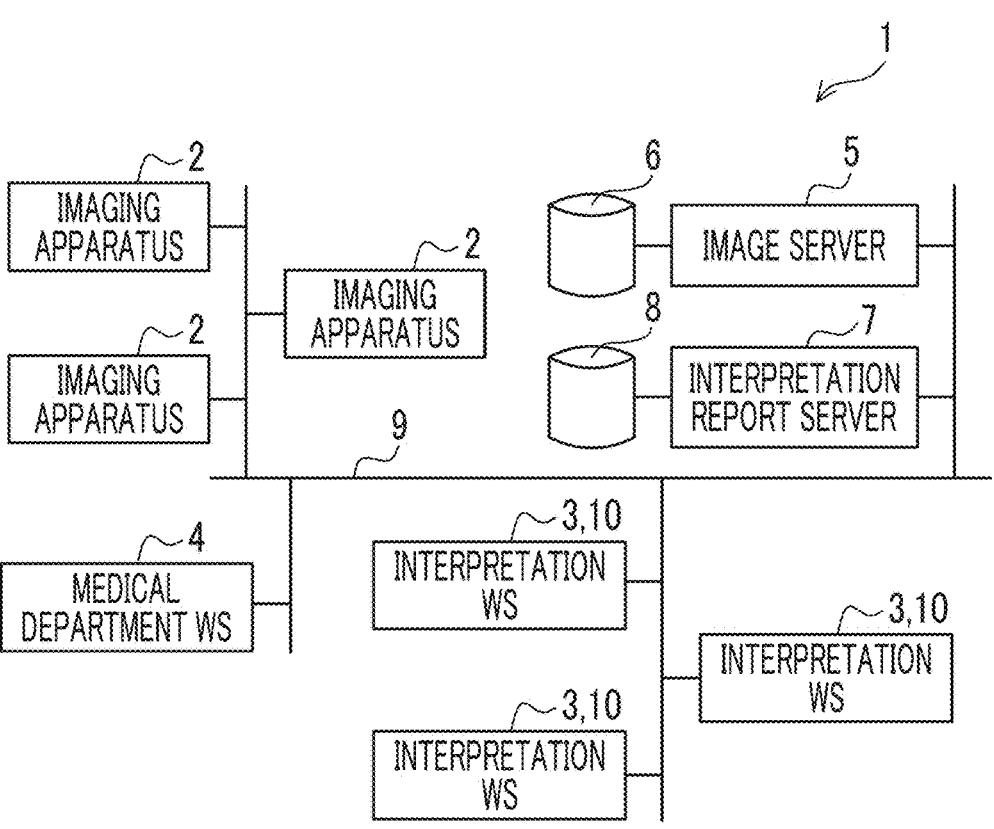
FIG. 1 is a block diagram showing a schematic configuration of a medical information system.

As shown in FIG. 1, the medical information system 1 according to the present embodiment includes a plurality of imaging apparatuses 2, a plurality of interpretation workstations (WS) 3 that are interpretation terminals, a medical department WS 4, an image server 5, an image database (DB) 6, an interpretation report server 7, and an interpretation report DB 8. The imaging apparatus 2, the interpretation WS 3, the medical department WS 4, the image server 5, and the interpretation report server 7 are connected to each other via a wired or wireless network 9 in a communicable state. In addition, the image DB 6 is connected to the image server 5, and the interpretation report DB 8 is connected to the interpretation report server 7.

The imaging apparatus 2 is an apparatus that generates a medical image showing a diagnosis target part of a subject by imaging the diagnosis target part. The imaging apparatus 2 may be, for example, a simple X-ray imaging apparatus, an endoscope apparatus, a computed tomography (CT) apparatus, a magnetic resonance imaging (MRI) apparatus, a positron emission tomography (PET) apparatus, and the like. A medical image generated by the imaging apparatus 2 is transmitted to the image server 5 and is saved therein.

The medical department WS 4 is a computer used by a doctor in the medical department for detailed observation of a medical image, viewing of an interpretation report, creation of an electronic medical record, and the like. In the medical department WS 4, each process such as creating an electronic medical record of a patient, requesting the image server 5 to view an image, and displaying a medical image received from the image server 5 is performed by executing a software program for each process. In addition, in the medical department WS 4, each process such as automatically detecting or highlighting suspected disease regions in the medical image, requesting to view an interpretation report from the interpretation report server 7, and displaying the interpretation report received from the interpretation report server 7 is performed by executing a software program for each process.

The image server 5 incorporates a software program that provides a function of a database management system (DBMS) to a general-purpose computer. In a case where the image server 5 receives a request to register a medical image from the imaging apparatus 2, the image server 5 prepares the medical image in a format for a database and registers the medical image in the image DB 6.

Image data representing the medical image acquired by the imaging apparatus 2 and accessory information attached to the image data are registered in the image DB 6. The accessory information includes information such as an image identification (ID) for identifying individual medical images, a patient ID for identifying a patient who is a subject, an examination ID for identifying examination content, and a unique identification (UID) assigned to each medical image, for example. In addition, the accessory information includes information such as an examination date when a medical image was generated, an examination time, the type of imaging apparatus used in the examination for acquiring the medical image, patient information (for example, a name, an age, and a gender of the patient), an examination part (that is, an imaging part), and imaging information (for example, an imaging protocol, an imaging sequence, an imaging method, imaging conditions, and whether or not a contrast medium is used), and a series number or collection number when a plurality of medical images are acquired in one examination. In addition, in a case where a viewing request from the interpretation WS 3 is received through the network 9, the image server 5 searches for a medical image registered in the image DB 6 and transmits the searched for medical image to the interpretation WS 3 that is a request source.

The interpretation report server 7 incorporates a software program for providing a function of DBMS to a general-purpose computer. In a case where the interpretation report server 7 receives a request to register an interpretation report from the interpretation WS 3, the interpretation report server 7 prepares the interpretation report in a format for a database and registers the interpretation report in the interpretation report database 8. Further, in a case where the request to search for the interpretation report is received, the interpretation report is searched for from the interpretation report DB 8.

In the interpretation report DB 8, for example, an interpretation report is registered in which information, such as an image ID for identifying a medical image to be interpreted, a radiologist ID for identifying an image diagnostician who performed the interpretation, a lesion name, position tion information of a lesion, findings, and a degree of certainty of the findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the Internet or a dedicated line. In any case, it is preferable that the network 9 has a configuration capable of realizing high-speed transmission of medical images such as an optical network.

The interpretation WS 3 requests the image server 5 to view a medical image, performs various types of image processing on the medical image received from the image server 5, displays the medical image, performs an analysis process on the medical image, highlights the medical image based on an analysis result, and creates an interpretation report based on the analysis result. In addition, the interpretation WS 3 supports creation of an interpretation report, requests the interpretation report server 7 to register and view an interpretation report, displays the interpretation report received from the interpretation report server 7, and the like. The interpretation WS 3 performs each of the above processes by executing a software program for each process. The interpretation WS 3 encompasses a document creation support apparatus 10, which will be described later, and in the above processes, processes other than those performed by the document creation support apparatus 10 are performed by a well-known software program, and therefore the detailed description thereof will be omitted here. In addition, processes other than the processes performed by the document creation support apparatus 10 may not be performed in the interpretation WS 3, and a computer that performs the processes may be separately connected to the network 9, and in response to a processing request from the interpretation WS 3, the requested process may be performed by the computer. Hereinafter, the document creation support apparatus 10 encompassed in the interpretation WS 3 will be described in detail.

Figure 2:
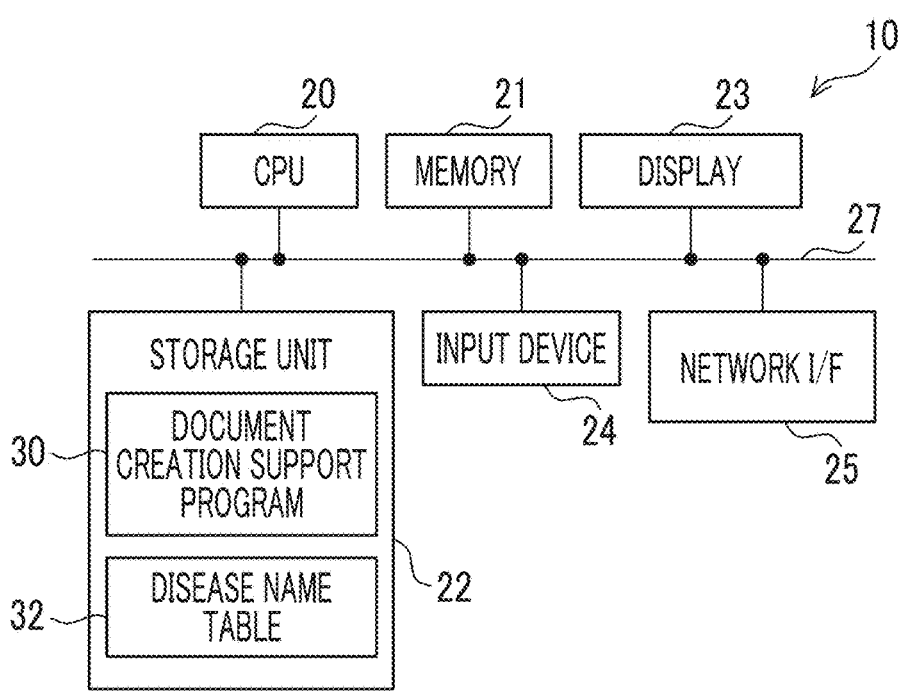
FIG. 2 is a block diagram showing an example of a hardware configuration of a document creation support apparatus.

Next, a hardware configuration of the document creation support apparatus 10 according to the present embodiment will be described with reference to FIG. 2. As shown in FIG. 2, the document creation support apparatus 10 includes a central processing unit (CPU) 20, a memory 21 as a temporary storage area, and a non-volatile storage unit 22. Further, the document creation support apparatus 10 includes a display 23 such as a liquid crystal display, an input device 24 such as a keyboard and a mouse, and a network interface (I/F) 25 connected to the network 9. The CPU 20, the memory 21, the storage unit 22, the display 23, the input device 24, and the network OF 25 are connected to a bus 27.

The storage unit 22 is realized by a hard disk drive (HDD), a solid state drive (SSD), a flash memory, or the like. A document creation support program 30 is stored in the storage unit 22 as a storage medium. The CPU 20 reads out the document creation support program 30 from the storage unit 22, loads the read document creation support program 30 into the memory 21, and executes the loaded document creation support program 30.

Figures 3, 4:
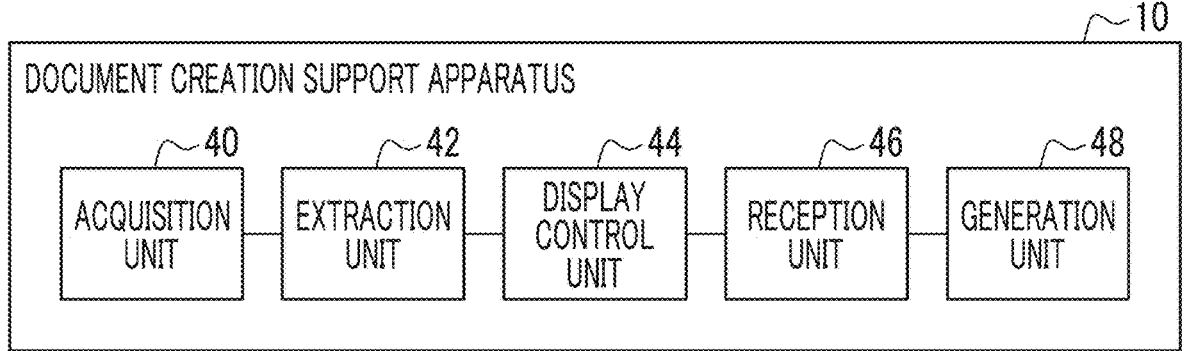
FIG. 3 is a diagram showing an example of a disease name table according to a first embodiment.
FIG. 4 is a block diagram showing an example of a functional configuration of a document creation support apparatus according to the first embodiment.

In addition, a disease name table 32 is stored in the storage unit 22. FIG. 3 shows an example of the disease name table 32. As shown in FIG. 3, the disease name table 32 includes a plurality of records in which combinations of organs and physical features included in the medical image and disease names are associated with each other. The disease name table 32 is an example of data in which physical features according to the disclosed technology and disease names are associated with each other.

Next, a functional configuration of the document creation support apparatus 10 according to the present embodiment will be described with reference to FIG. 4. As shown in FIG. 4, the document creation support apparatus 10 includes an acquisition unit 40, an extraction unit 42, a display control unit 44, a reception unit 46, and a generation unit 48. The CPU 20 executes the document creation support program 30 to function as the acquisition unit 40, the extraction unit 42, the display control unit 44, the reception unit 46, and the generation unit 48.

The acquisition unit 40 acquires a medical image to be diagnosed (hereinafter referred to as a "diagnosis target image") from the image server 5 via the network I/F 25.

The extraction unit 42 extracts regions having one or more preset physical features from the diagnosis target image acquired by the acquisition unit 40. In the present embodiment, the extraction unit 42 extracts a region having physical features from the diagnosis target image using a trained model M1 for extracting the region having the physical features from the diagnosis target image.

The trained model M1 is configured by, for example, a convolutional neural network (CNN) that receives a medical image as an input and outputs a region having physical features included in the medical image. The trained model M1 is a model trained by machine learning using a large number of medical images in which a region having physical features is known as training data.

Examples of a region having physical features include a region of which a pixel value is within a set range in advance. Specifically, for example, as a region of which a pixel value is within a set range in advance, a region of which a pixel value is relatively close to a preset value as compared with the surroundings can be mentioned. More specifically, as a region of which a pixel value is relatively close to a preset value as compared with the surroundings, for example, a region of a mass that is relatively white compared with the surroundings, a region of a mass that is relatively dark compared with the surroundings, and the like can be mentioned.

In addition, examples of the region having physical features include a region of a shape having preset features. Specifically, examples of the region of a shape having preset features include a protruded region, an uneven-shaped region having an irregular margin, and the like.

The physical features described above are features useful for the evaluation of a disease. In addition, some of the features useful for the evaluation of the disease are organ-specific. For example, in a CT image, a region of a mass that is relatively white compared with the surroundings in the brain is suspected of having cerebral hemorrhage. In addition, for example, in a CT image, a region of a mass that is relatively dark compared with the surroundings in the brain is suspected of having cerebral infarction. In addition, for example, in an endoscopic image, a protruded region in the large intestine is suspected of having a colon polyp. Further, for example, in a CT image, an uneven-shaped region having an irregular margin in the liver is suspected of having a liver cirrhosis.

Therefore, the trained model M1 according to the present embodiment is prepared for each combination of organs and physical features. In other words, the physical features to be extracted are set in advance for each organ. The extraction unit 42 extracts regions having one or more physical features from the diagnosis target image by inputting the diagnosis target image into the trained model M1 prepared corresponding to the organ included in the diagnosis target image.

Figure 5:
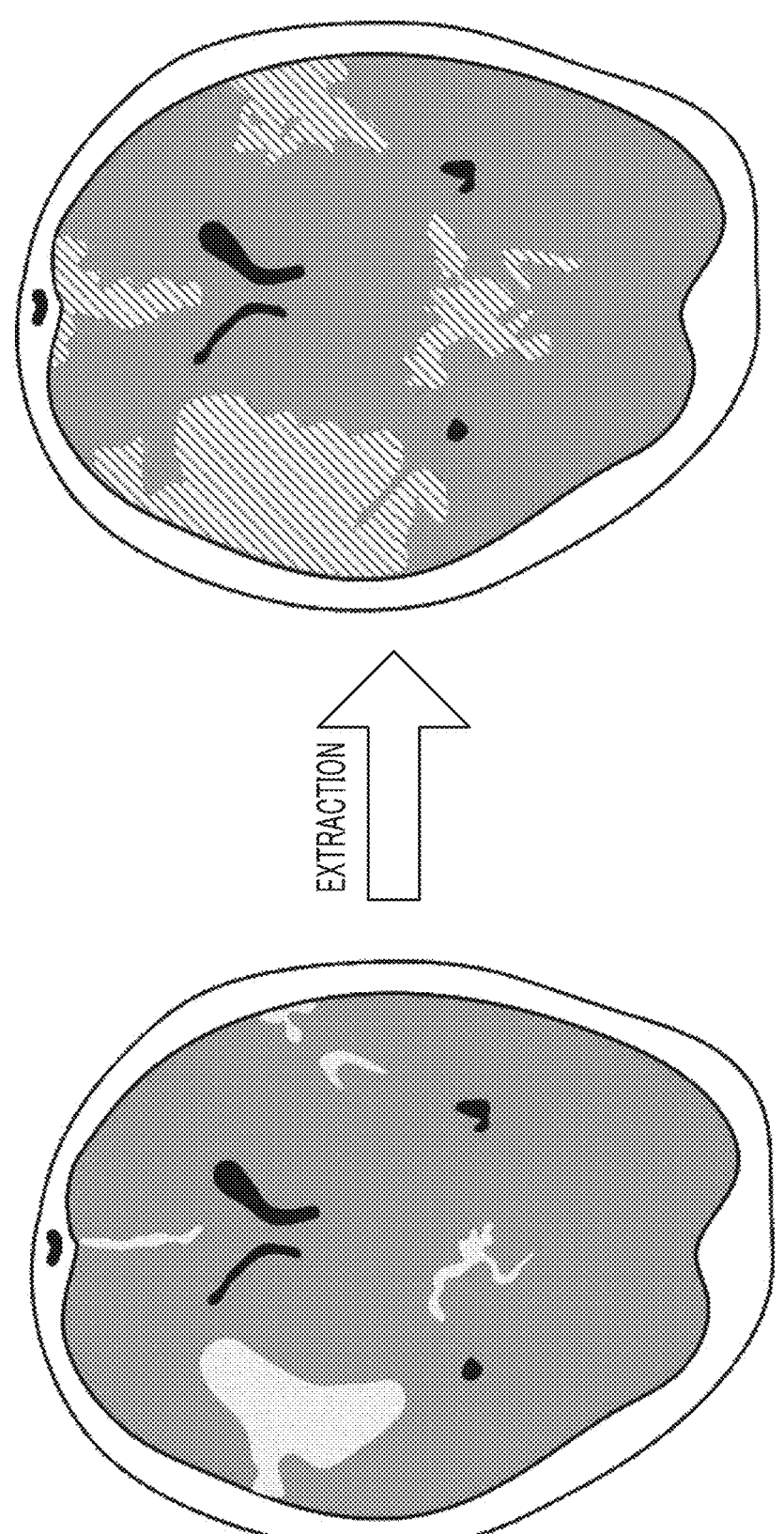
FIG. 5 is a diagram showing an example of an extraction result of a region having a physical feature.

FIG. 5 shows an example of the extraction result from the extraction unit 42. FIG. 5 shows an example in which a region of a mass that is relatively white compared with the surroundings is extracted from a CT image of the brain. In the example of FIG. 5, the region filled with the diagonal line indicates a region of a mass that is relatively white compared with the surroundings. In this way, by using the trained model M1, it is possible to extract a region having physical features that are difficult for the human eye to ascertain.

The display control unit 44 performs control to display information indicating a region extracted by the extraction unit 42 on the display 23. Specifically, the display control unit 44 performs control to highlight the region extracted by the extraction unit 42 by filling the region extracted by the extraction unit 42 in the diagnosis target image with a preset color. By this control, for example, a diagnosis target image in which the region filled with the diagonal line in FIG. 5 is filled with light blue is displayed on the display 23. At the time of this control, in a case where a plurality of regions having different physical features are extracted by the extraction unit 42, the display control unit 44 may display the physical features in an identifiable manner by making colors different for each physical feature. In addition, the display control unit 44 may perform control to highlight a region extracted by the extraction unit 42 by drawing, for example, an outer edge of the region with a line of a preset color. In addition, for example, the display control unit 44 may control to highlight a region extracted by the extraction unit 42 by surrounding the region with a bounding box.

In a CT image including a plurality of slice images, in a case where one slice image is present as a region extracted by the extraction unit 42, the display control unit 44 may perform control to display information indicating the region extracted by the extraction unit 42 on the display 23 for the slice image. In this case, in a case where a plurality of slice images having one region are present, the display control unit 44 may perform control to display information indicating the region extracted by the extraction unit 42 on the display 23 for the slice image having the largest area for one region.

In addition, the display control unit 44 performs control to display a comment on findings generated by the generation unit 48, which will be described later, on the display 23.

A user, such as a doctor, selects a region for creating an interpretation report from among the regions having physical features displayed on the display 23 via the input device 24. The reception unit 46 receives information indicating the region selected by the user from among the regions extracted by the extraction unit 42.

The generation unit 48 refers to the disease name table 32 and generates a comment on findings using a disease name associated with a physical feature of the region received by the reception unit 46, that is, the region selected by the user. Specifically, the generation unit 48 refers to the disease name table 32, and acquires a disease name associated with a combination of physical features of the organ included in the diagnosis target image and the region received by the reception unit 46. Then, the generation unit 48 generates a comment on findings using the acquired disease name. Examples of comments on findings regarding the brain include "Intracranial bleeding is found", "Subarachnoid hemorrhage is found", and "Cerebral infarction is found". For example, the generation unit 48 generates a comment on findings by inputting a disease name to a recurrent neural network trained to generate text from input words. The user creates an interpretation report based on the comment on findings generated by the generation unit 48 and displayed on the display 23 under the control of the display control unit 44.

In addition, the generation unit 48 may generate a plurality of comments on findings for one disease name. In this case, for example, for the lung included in the diagnosis target image, the generation unit 48 may generate a plurality of comments on findings with different combinations of property items such as "Tumor is found in the left upper lobe" and "4.2 cm-sized tumor with pleural invagination is found in the left upper lobe" for one disease name "tumor" corresponding to the region selected by the user. In addition, in this case, for example, the generation unit 48 may generate a plurality of comments on findings with the same meaning such as "Partially solid tumor is found in the left upper lobe" and "Tumor of which the center is solid and the periphery is frosted glass is found in the left upper lobe" but with different expressions for one disease name "tumor".

Figure 6:
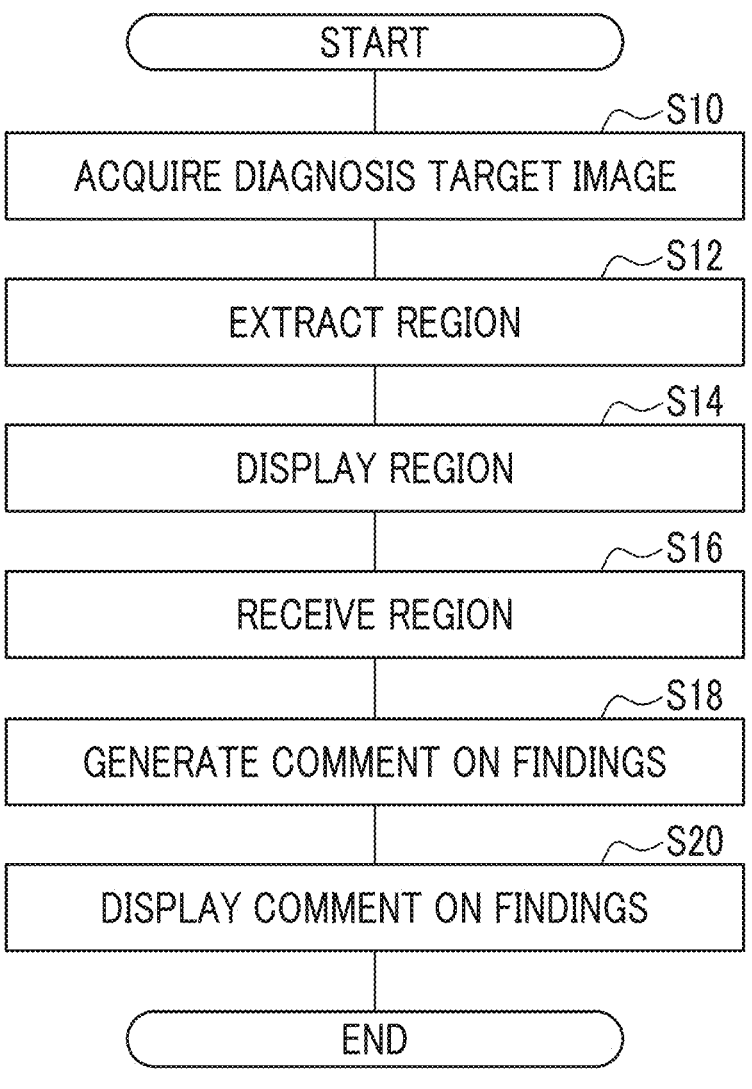
FIG. 6 is a flowchart showing an example of a document creation support process according to the first embodiment.

Next, with reference to FIG. 6, operations of the document creation support apparatus 10 according to the present embodiment will be described. The CPU 20 executes the document creation support program 30, whereby a document creation support process shown in FIG. 6 is executed. The document creation support process shown in FIG. 6 is executed, for example, in a case where an instruction to start execution is input by the user.

In Step S10 of FIG. 6, the acquisition unit 40 acquires the diagnosis target image from the image server 5 via the network I/F 25. In Step S12, as described above, the extraction unit 42 extracts regions having one or more preset physical features from the diagnosis target image acquired in Step S10 by using the trained model M1. In Step S14, as described above, the display control unit 44 performs control to display information indicating the region extracted in Step S12 on the display 23.

In Step S16, the reception unit 46 receives information indicating the region selected by the user from among the regions extracted in Step S12. In Step S18, as described above, the generation unit 48 refers to the disease name table 32 and generates a comment on findings using the disease name associated with the physical feature of the region received in Step S16. In Step S20, the display control unit 44 performs control to display the comment on findings generated in Step S18 on the display 23. In a case where the process of Step S20 ends, the document creation support process ends.

As described above, according to the present embodiment, it is possible to easily support the generation of the interpretation report.

Second Embodiment

A second embodiment of the disclosed technology will be described. Since the configuration of the medical information system 1 and the hardware configuration of the document creation support apparatus 10 according to the present embodiment are the same as those of the first embodiment, the description thereof will be omitted.

In the disease name table 32 according to the present embodiment, a plurality of disease names are associated with one physical feature. Specifically, for example, two disease names, "cerebral hemorrhage" and "brain tumor," are associated with the physical feature of the organ called "brain" and "a mass that is relatively white compared with the surroundings".

Figures 7, 8:
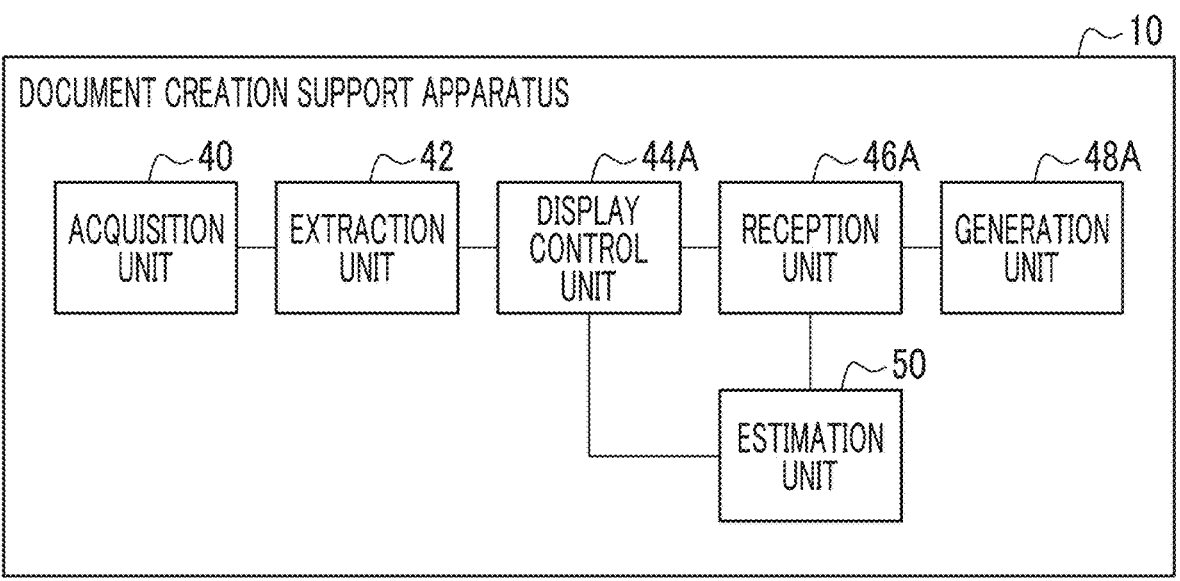
FIG. 7 is a block diagram showing an example of a functional configuration of a document creation support apparatus according to a second embodiment.
FIG. 8 is a diagram showing a display example of a plurality of comments on findings.

A functional configuration of the document creation support apparatus 10 according to the present embodiment will be described with reference to FIG. 7. The same reference numerals are assigned to the functional units having the same functions as the document creation support apparatus 10 according to the first embodiment, and the description thereof will be omitted. As shown in FIG. 7, the document creation support apparatus 10 includes an acquisition unit 40, an extraction unit 42, a display control unit 44A, a reception unit 46A, a generation unit 48A, and an estimation unit 50. The CPU 20 executes the document creation support program 30 to function as the acquisition unit 40, the extraction unit 42, the display control unit 44A, the reception unit 46A, the generation unit 48A, and the estimation unit 50.

Similarly to the display control unit 44 according to the first embodiment, the display control unit 44A performs control to display information indicating the region extracted by the extraction unit 42 on the display 23.

In addition, the display control unit 44A performs control to display a plurality of comments on findings generated by the generation unit 48A, which will be described later, on the display 23. At the time of this control, the display control unit 44A controls a display mode of the plurality of comments on findings generated by the generation unit 48A based on an estimation result of the disease name by the estimation unit 50, which will be described later.

Specifically, the display control unit 44A performs control to display, on the display 23, the comment on findings including the disease name estimated by the estimation unit 50 among the plurality of comments on findings generated by the generation unit 48A with a higher priority than the comment on findings not including the disease name estimated by the estimation unit 50. As a specific example, a case will be described in which there are two comments on findings generated by the generation unit 48A, "Cerebral hemorrhage is found" and "Brain tumor is found" and the disease name estimated by the estimation unit 50 is "brain tumor". In this case, as shown in FIG. 8 as an example, the display control unit 44A increases the priority of the comment on findings including "brain tumor" by performing control to display the comment on findings including "brain tumor" above the comment on findings not including "brain tumor". In addition, for example, the display control unit 44A may make the size of the character of the comment on findings including the disease name estimated by the estimation unit 50 larger than the size of the character of the comment on findings not including the disease name estimated by the estimation unit 50. In addition, for example, the display control unit 44A may perform control to display a plurality of comments on findings generated by the generation unit 48A on the display 23 in predetermined colors according to the priority. In addition, for example, the display control unit 44A may perform control to display only the comment on findings including the disease name estimated by the estimation unit 50 on the display 23 among the plurality of comments on findings generated by the generation unit 48A.

Similarly to the reception unit 46 according to the first embodiment, the reception unit 46A receives information indicating the region selected by the user from among the regions extracted by the extraction unit 42. In addition, the reception unit 46A receives the comment on findings selected by the user from among the plurality of comments on findings displayed on the display 23 under the control of the display control unit 44A. This received comment on findings is used to create an interpretation report.

The generation unit 48A refers to the disease name table 32 and generates a plurality of comments on findings using a plurality of disease names associated with physical features of the region received by the reception unit 46A, that is, the region selected by the user. Specifically, the generation unit 48A refers to the disease name table 32, and acquires a plurality of disease names associated with a combination of physical features of the organ included in the diagnosis target image and the region received by the reception unit 46A. Then, the generation unit 48A generates a plurality of comments on findings using the plurality of acquired disease name. For example, the generation unit 48A generates a plurality of comments on findings by inputting disease names to a recurrent neural network trained to generate text from input words.

In addition, the generation unit 48A may derive a recommendation level of the comment on findings for each of the plurality of generated comments on findings. In this case, for example, the generation unit 48A derives the recommendation level of the comment on findings based on an image of a region portion received by the reception unit 46A in the diagnosis target image, a plurality of generated comments on findings, and a trained model M3 that has been trained in advance. The trained model M3 is, for example, a machine learning model that has been trained in advance using training data including an image of a region portion received by the reception unit 46A in the diagnosis target image, a plurality of comments on findings, and a recommendation level for each of the plurality of comments on findings. In a case where an image of the region portion received by the reception unit 46A in the diagnosis target image and a plurality of comments on findings generated by the generation unit 48A are input to the trained model M3, the recommendation level for each of the plurality of comments on findings is output. The trained model M3 includes a CNN, for example. In this form example, the display control unit 44A may perform control to display the recommendation level derived for each of the plurality of comments on findings, together with the plurality of comments on findings generated by the generation unit 48A.

The estimation unit 50 estimates a disease name using the diagnosis target image. Specifically, the estimation unit 50 estimates a disease name based on an image of a region portion received by the reception unit 46A in the diagnosis target image, an image of a region portion having physical features in the medical image for learning, and a trained model M2 that has been trained in advance using the training data including the disease name of the disease included in the image of the region portion. In a case where an image of the region portion received by the reception unit 46A in the diagnosis target image is input to the trained model M2, the disease name is output. The trained model M2 includes a CNN, for example.

The estimation unit 50 may estimate the disease name based on the degree of similarity between the diagnosis target image and the image prepared in advance for each disease. As the degree of similarity of the images in this case, for example, a distance of a feature amount vector obtained by vectorizing a plurality of feature amounts extracted from the image can be applied. In this case, the estimation unit 50 uses the disease name of the image having the highest degree of similarity to the image of the region portion received by the reception unit 46A of the diagnosis target image as the estimation result.

Further, in the case of a liver cyst, the CT values of the portion of the liver cyst are often uniform at 10 to 40. In addition, in the case of a liver tumor, the CT values of the portion of the liver tumor often have a large variance. Therefore, the estimation unit 50 may estimate the disease name based on the statistical value of the pixel value in the region extracted from the diagnosis target image. Examples of the statistical value in this case include at least one of the average value, the standard deviation, the variance, the maximum brightness value, or the minimum brightness value.

Figure 9:
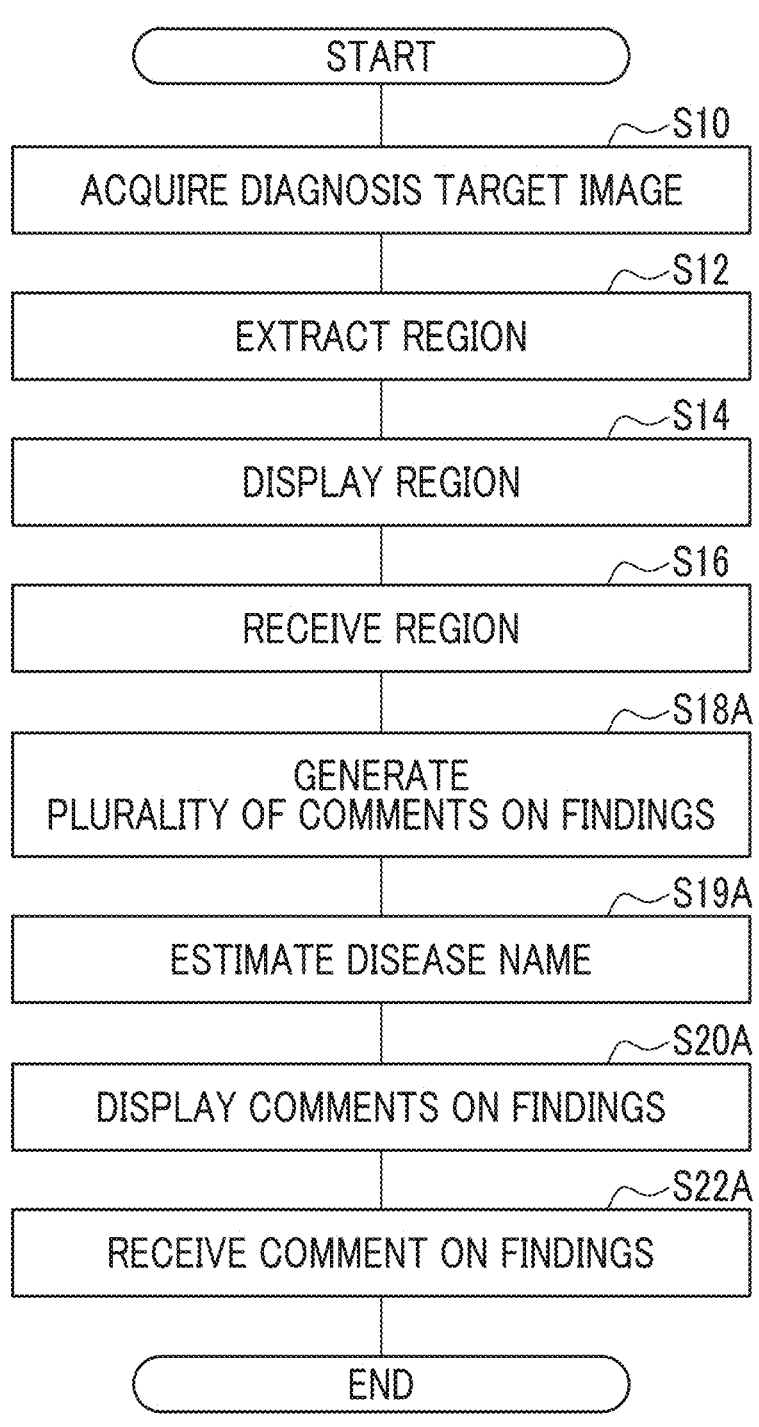
FIG. 9 is a flowchart showing an example of a document creation support process according to the second embodiment.

Next, with reference to FIG. 9, operations of the document creation support apparatus 10 according to the present embodiment will be described. The CPU 20 executes the document creation support program 30, whereby a document creation support process shown in FIG. 9 is executed. The document creation support process shown in FIG. 9 is executed, for example, in a case where an instruction to start execution is input by the user. Steps in FIG. 9 that execute the same processing as in FIG. 6 are given the same step numbers and descriptions thereof will be omitted.

In Step S18A of FIG. 9, as described above, the generation unit 48A refers to the disease name table 32 and generates a plurality of comments on findings using the plurality of disease names associated with the physical feature of the region received in Step S16. In Step S19A, as described above, the estimation unit 50 estimates the disease name using the diagnosis target image acquired in Step S10.

In Step 520A, the display control unit 44A performs control to display the plurality of comments on findings generated in Step S18A on the display 23. At the time of this control, as described above, the display control unit 44A controls the display mode of the plurality of comments on findings generated in Step S18A based on the estimation result of the disease name in Step S19A. In Step S22A, the reception unit 46A receives the comment on findings selected by the user from among the plurality of comments on findings displayed on the display 23 in Step 520A. This received comment on findings is used to create an interpretation report. In a case where the process of Step S22A ends, the document creation support process ends.

As described above, according to the present embodiment, the same effect as the first embodiment can be obtained.

Third Embodiment

A third embodiment of the disclosed technology will be described. Since the configuration of the medical information system 1 and the hardware configuration of the document creation support apparatus 10 according to the present embodiment are the same as those of the first embodiment, the description thereof will be omitted. Also, since the disease name table 32 according to the present embodiment is the same as that of the second embodiment, the description thereof will be omitted.

Figure 10:
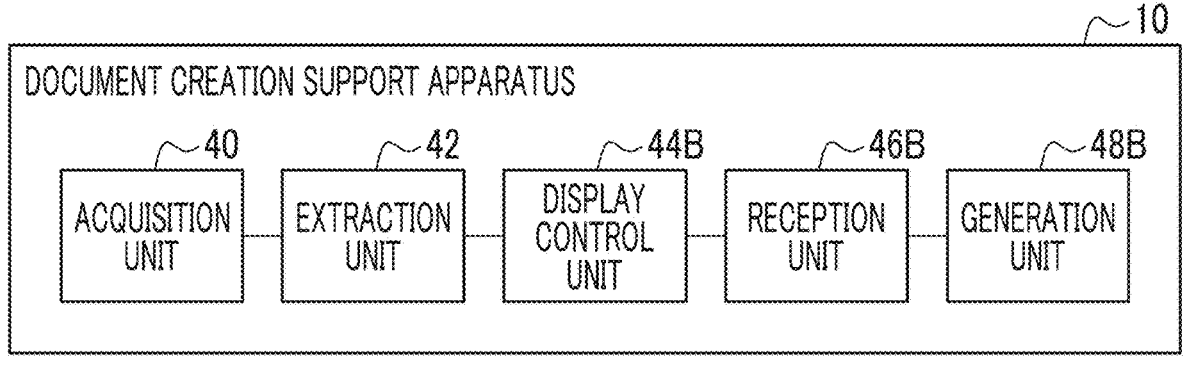
FIG. 10 is a block diagram showing an example of a functional configuration of a document creation support apparatus according to a third embodiment.

A functional configuration of the document creation support apparatus 10 according to the present embodiment will be described with reference to FIG. 10. The same reference numerals are assigned to the functional units having the same functions as the document creation support apparatus 10 according to the first embodiment, and the description thereof will be omitted. As shown in FIG. 10, the document creation support apparatus 10 includes an acquisition unit 40, an extraction unit 42, a display control unit 44B, a reception unit 46B, and a generation unit 48B. The CPU 20 executes the document creation support program 30 to function as the acquisition unit 40, the extraction unit 42, the display control unit 44B, the reception unit 46B, and the generation unit 48B.

The display control unit 44B performs control to display information indicating a region extracted by the extraction unit 42 on the display 23. In addition, the display control unit 44B performs control to display a plurality of comments on findings generated by the generation unit 48B, which will be described later, on the display 23.

In addition, the display control unit 44B performs control to display, in an identifiable manner, a status for the region extracted by the extraction unit 42 among a plurality of statuses related to creation work of a medical document by a user. An example of a medical document includes an interpretation report. In the present embodiment, an example will be described in which the following four statuses are applied as a plurality of statuses related to creation work of a medical document.

A first status is a status in which the user has not confirmed the region extracted by the extraction unit 42. A second status is a status in which the user has designated that the region extracted by the extraction unit 42 is the target of the creation work of the medical document, and the creation work is incomplete. A third status is a status in which the user has designated that the region extracted by the extraction unit 42 is excluded from the creation work of the medical document. A fourth status is a status in which the creation work of the medical document for the region extracted by the extraction unit 42 has been completed. Note that the plurality of statuses may be two or three of these four statuses.

The display control unit 44B performs control to display the first status in an identifiable manner in the control of first displaying the information indicating the region extracted by the extraction unit 42 on the display 23. Specifically, for example, the display control unit 44B performs control to display the diagnosis target image on the display 23 in a state where the region extracted by the extraction unit 42 in the diagnosis target image is filled with a preset color. Note that, at the time of this control, in a case where a plurality of regions having different physical features are extracted by the extraction unit 42, the display control unit 44B may display the physical features in an identifiable manner by making colors different for each physical feature.

In a case where an operation in which a region is designated by the user and the status of the designated region is set as the second status is performed, the display control unit 44B performs control to display the second status in an identifiable manner by adding a predetermined mark to the region. Accordingly, a region which is designated by the user as a target for creating the medical document but in which the creation of the medical document has not been completed is conspicuous, so that it is possible to suppress omission of the creation of the medical document.

In a case where an operation in which a region is designated by the user and an instruction for displaying the comment on findings is provided is performed, the display control unit 44B performs control to display, on the display 23, a plurality of comments on findings generated by the generation unit 48B, which will be described later, for the region. FIG. 11 shows an example of a comment-on-findings display screen displayed on the display 23 by this control. As shown in FIG. 11, on the comment-on-findings display screen, a plurality of comments on findings, a button designated in a case where the user selects each comment on findings, and a button designated in a case where the user determines that there is no finding are displayed. In a case where the user performs an operation of selecting one comment on findings from a plurality of comments on findings on the comment-on-findings display screen, the display control unit 44B performs control to display the fourth status in an identifiable manner by canceling the filling of the region and drawing the outer edge of the region with lines of a predetermined color.

FIG. 12 shows another example of the comment-on-findings display screen. FIG. 11 is an example in a case where a region having physical features is extracted in the liver, and FIG. 12 is an example in a case where the shape of the liver itself has physical features.

In a case where an operation in which a region is designated by the user and the status of the designated region is set as the third status is performed, the display control unit 44B performs control to display the third status in an identifiable manner by graying out the region. An example of this operation includes an operation in which the user designates a no-finding button on the comment-on-findings display screen shown in FIG. 11, for example.

Figure 13:
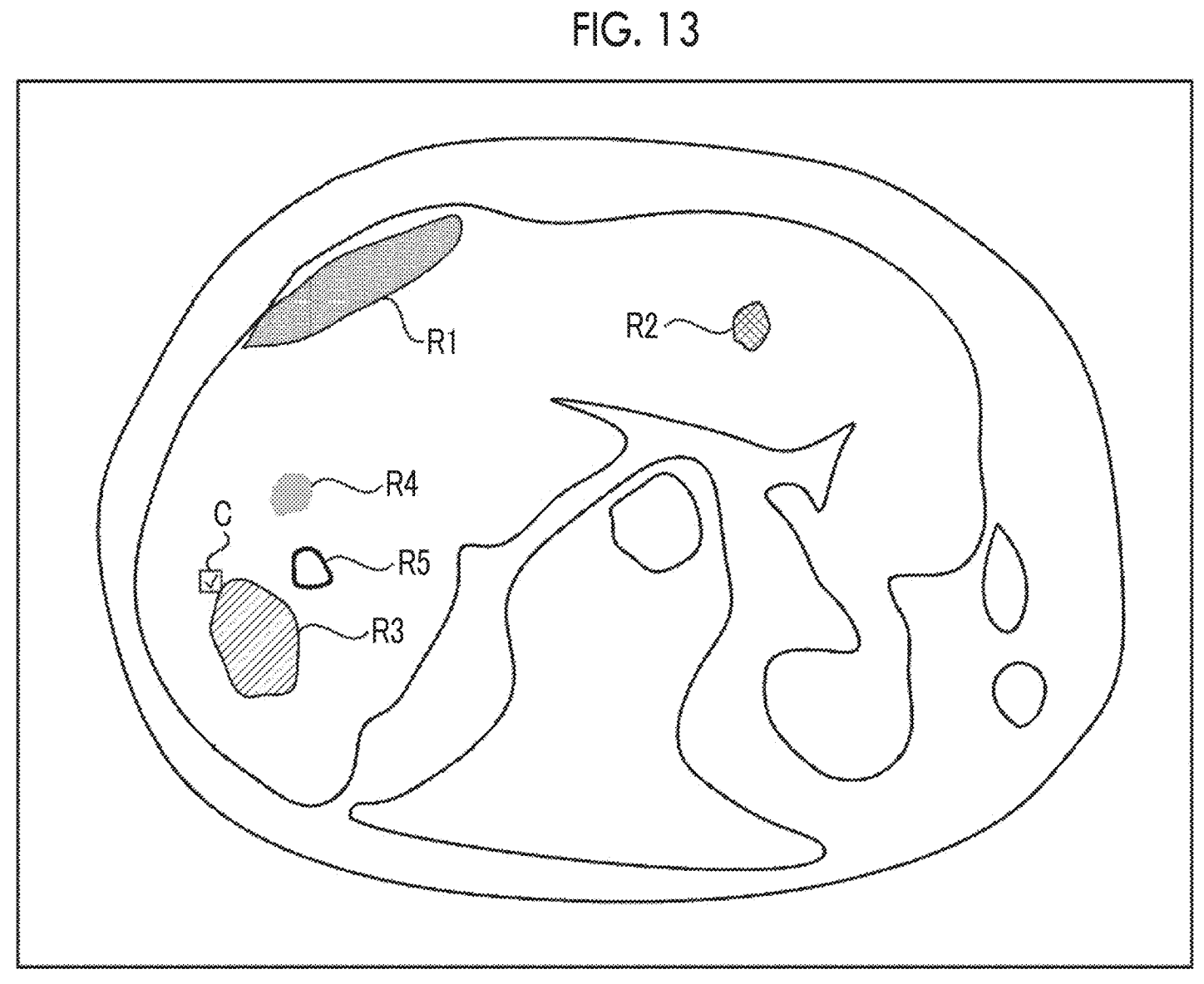

FIG. 13 shows an example of a status display screen displayed on the display 23 under the control of the display control unit 44B. FIG. 13 shows an example in which a CT image of a liver is applied as a diagnosis target image. FIG. 13 shows an example in which the statuses of a region R1 and a region R2 are the first status, and the status of a region R3 is the second status. A check mark C is added to region R3 as a predetermined mark. FIG. 13 shows an example in which the status of a region R4 is the third status and a status of the region R5 is the fourth status.

Note that the method of displaying the first status to the fourth status in an identifiable manner is not limited to the above example. For example, the first to fourth statuses may be displayed in an identifiable manner by the line type or thickness of the contour of the region, the transparency or pattern of the filling of the region, the blinking of the region, the animation display of the region, the addition of different marks, and the like. Also, the mark is not limited to the check mark, and may be an arrow or a symbol such as "+".

The reception unit 46B receives information indicating the region selected by the user from among the regions extracted by the extraction unit 42. In addition, the reception unit 46B receives an operation indicating which of the four statuses is set for the selected region. In addition, the reception unit 46B receives the comment on findings selected by the user from among the plurality of comments on findings displayed on the display 23 under the control of the display control unit 44B. This received comment on findings is used to create an interpretation report.

Similarly to the generation unit 48A according to the second embodiment, the generation unit 48B refers to the disease name table 32 and generates a plurality of comments on findings using a plurality of disease names associated with physical features of the region received by the reception unit 46B. In addition, similarly to the generation unit 48 according to the first embodiment, the generation unit 48B may generate one comment on findings using one disease name associated with physical features of the region received by the reception unit 46B.

Figure 14:
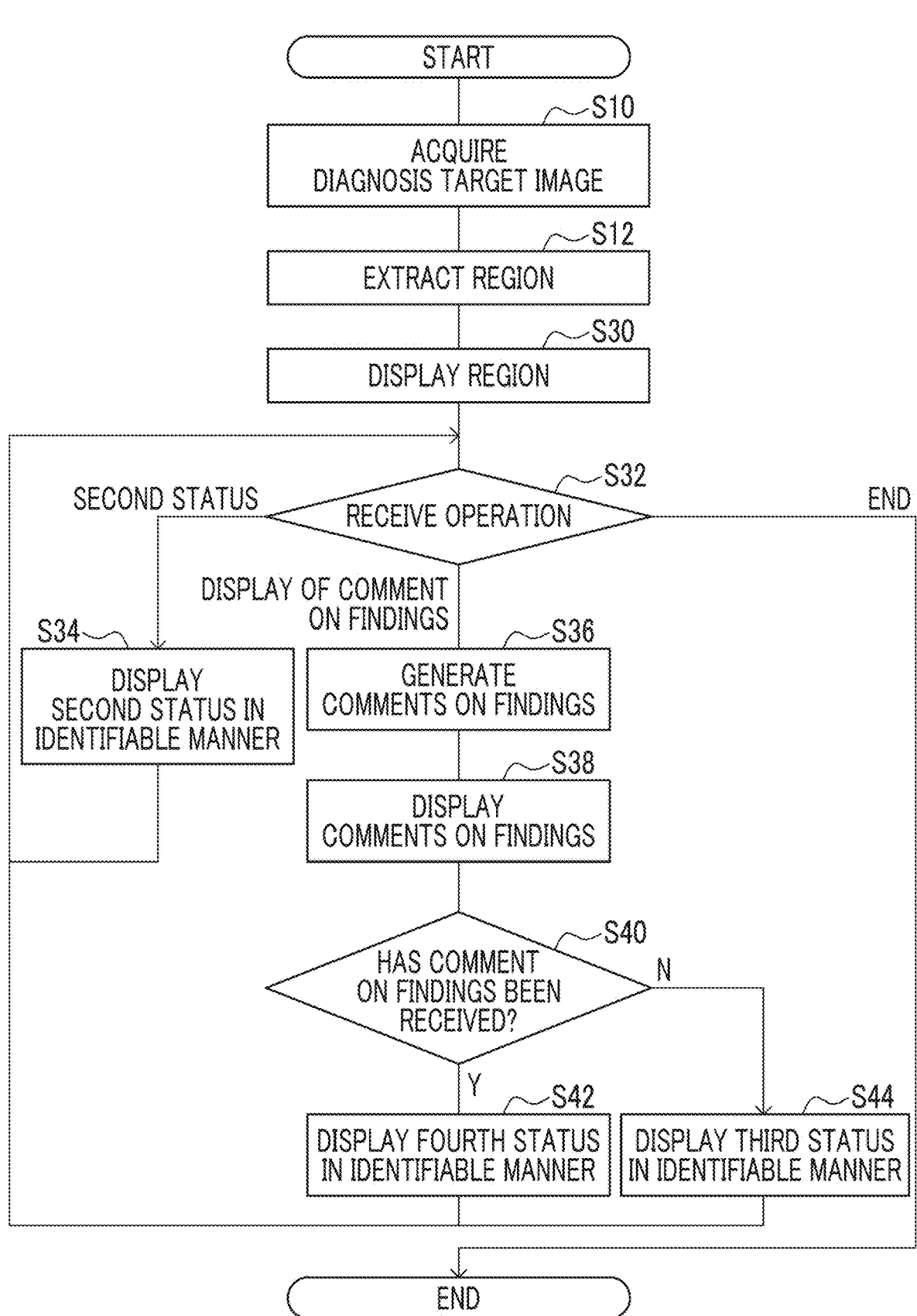
FIG. 14 is a flowchart showing an example of a document creation support process according to the third embodiment.

Next, with reference to FIG. 14, operations of the document creation support apparatus 10 according to the present embodiment will be described. The CPU 20 executes the document creation support program 30, whereby a document creation support process shown in FIG. 14 is executed. The document creation support process shown in FIG. 14 is executed, for example, in a case where an instruction to start execution is input by the user. Steps in FIG. 14 that execute the same processing as in FIG. 9 are given the same step numbers and descriptions thereof will be omitted.

In Step S30 of FIG. 14, the display control unit 44B performs control to display information indicating the region extracted in Step S12 on the display 23. At the time of this control, as described above, the display control unit 44B performs control to display the status of each region to be identifiable as the first status. In Step S32, the reception unit 46B receives an operation by the user. In a case where the operation received by the reception unit 46B in Step S32 is an operation in which a region is designated by the user and the status of the designated region is set as the second status, the process proceeds to Step S34.

In Step S34, the display control unit 44B performs control to display the second status in an identifiable manner by adding a predetermined mark to the region designated by the user. In a case where the process of Step S34 ends, the process returns to Step S32.

In a case where the operation received by the reception unit 46B in Step S32 is an operation in which a region is designated by the user and an instruction for displaying the comment on findings is provided, the process proceeds to Step S36. In Step S36, as described above, the generation unit 48B refers to the disease name table 32 and generates a plurality of comments on findings using the plurality of disease names associated with the physical feature of the region designated by the user.

In Step S38, the display control unit 44B performs control to display the plurality of comments on findings generated in Step S36 on the display 23 for the region designated by the user. In Step S40, the reception unit 46B determines whether or not the comment on findings selected by the user from among the plurality of comments on findings displayed on the display 23 in Step S38 has been received. In a case where this determination is affirmative, the process proceeds to Step S42. In Step S42, the display control unit 44B performs control to display the fourth status in an identifiable manner by canceling the filling of the region designated by the user and drawing the outer edge of the region with lines of a predetermined color. In a case where the process of Step S42 ends, the process returns to Step S32.

In a case where the operation received by the reception unit 46B in Step S40 is an operation in which a region is designated by the user and the status of the designated region is set as the third status, the determination in Step S40 is a negative determination, and the process proceeds to Step S44. In Step S44, the display control unit 44B performs control to display the third status in an identifiable manner by graying out the region designated by the user. In a case where the process of Step S44 ends, the process returns to Step S32.

In a case where the operation received by the reception unit 46B in Step S32 is an operation to end the display of the screen, the document creation support process ends.

As described above, according to the present embodiment, the same effect as the first embodiment can be obtained. Moreover, according to the present embodiment, the user can easily ascertain the progress of the work.

Figure 15:
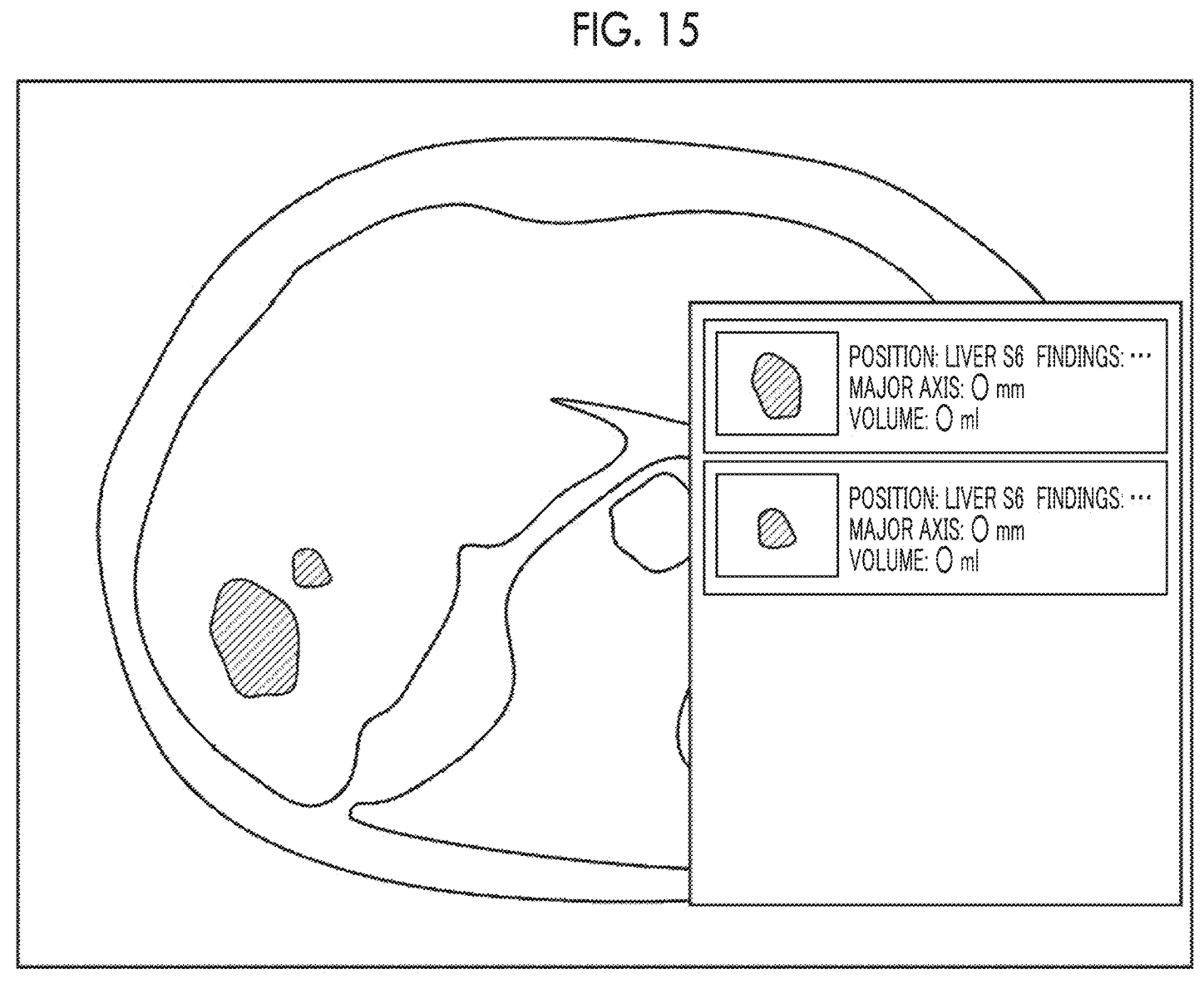

In each of the above-described embodiments, as shown in FIG. 15 as an example, the display control units 44, 44A, and 44B may perform control to display a list of information regarding each of the plurality of regions extracted by the extraction unit 42 in a case where the user performs an operation to instruct display of the list. In addition, in a case of performing the control of displaying the list in the third embodiment, the display control unit 44B may perform control to display the list of the information regarding each of the plurality of regions extracted by the extraction unit 42 for each status. In addition, the user may select a region for creating the interpretation report from among the plurality of regions displayed in a list on the display 23 via the input device 24.

In addition, in each of the above-described embodiments, a case where the generation units 48, 48A, and 48B generate the comment on findings for the region selected by the user from among the regions extracted by the extraction unit 42 has been described, but the present disclosure is not limited thereto. The generation units 48, 48A, and 48B may be configured to generate the comment on findings for all the regions extracted by the extraction unit 42.

In addition, in each of the above-described embodiments, a case where the extraction unit 42 extracts a region having physical features from the diagnosis target image using the trained model M1 has been described, but the present disclosure is not limited thereto. For example, the extraction unit 42 may be configured to extract a region that satisfies a condition set in advance in the diagnosis target image as a region having physical features. Examples of the region that satisfies the condition in this case include a region in which the CT value is equal to or greater than a first threshold value and the area is equal to or greater than a second threshold value. In addition, examples of the region that satisfies the condition in this case include a region in which the CT value is less than a third threshold value and the area is equal to or greater than the second threshold value. In addition, examples of the region that satisfies the condition in this case include a region in which the CT value is within a certain percentage in which the frequency of the histogram is higher and the area is equal to or greater than the second threshold value. Moreover, the condition in this case may be set for each organ, for example.

Further, in this case, as shown in FIG. 16 as an example, the display control units 44, 44A, and 44B may perform control to display, on the display 23, information indicating under which conditions each of the plurality of regions extracted by the extraction unit 42 is extracted. FIG. 16 shows an example of a region extracted according to the condition that each region has a low brightness in the liver and has a size equal to or larger than a certain area, that is, a region in which the CT value of the liver is less than the third threshold value and an area is equal to or greater than the second threshold value.

In addition, in each of the above-described embodiments, in a case where the user corrects the disease name for the region extracted by the extraction unit 42, the document creation support apparatus 10 may add, to the disease name table 32, a record that associates the physical features of the region with the disease name corrected by the user.

Further, in each of the above-described embodiments, for example, as a hardware structure of a processing unit that executes various kinds of processing, such as each functional unit of the document creation support apparatus 10, the following various processors can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example in which a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

In the above embodiment, the document creation support program 30 has been described as being stored (installed) in the storage unit 22 in advance; however, the present disclosure is not limited thereto. The document creation support program 30 may be provided in a form recorded in a recording medium such as a compact disc read only memory (CD-ROM), a digital versatile disc read only memory (DVD-ROM), and a universal serial bus (USB) memory. In addition, the document creation support program 30 may be configured to be downloaded from an external device via a network.

The disclosures of Japanese Patent Application No. 2021-068674 filed on Apr. 14, 2021 and Japanese Patent Application No. 2021-208523 filed on Dec. 22, 2021 are incorporated herein by reference in their entirety. In addition, all literatures, patent applications, and technical standards described herein are incorporated by reference to the same extent as if the individual literature, patent applications, and technical standards were specifically and individually stated to be incorporated by reference.

What is claimed is:

1. A document creation support apparatus comprising at least one processor, wherein the processor is configured to:

extract regions having one or more preset physical features from a medical image according to a brightness condition of each of the regions, wherein a pixel value of each of the regions is within a set range;

perform control to display information indicating the extracted region, wherein the information indicating the extracted region comprises at least information indicating under which brightness condition each of the plurality of regions is extracted;

receive information indicating a selected region from among the extracted regions;

access a memory to refer to a disease name table in which the physical features and disease names are associated with each other; and generate a comment on findings using a disease name associated with a physical feature of the selected region.

2. The document creation support apparatus according to claim 1, wherein the processor is configured to extract, from the medical image, a region of a shape having a set feature as the region having the physical feature.

3. The document creation support apparatus according to claim 1, wherein the physical feature is set for each organ.

4. The document creation support apparatus according to claim 1, wherein a plurality of disease names are associated with the physical feature.

5. The document creation support apparatus according to claim 1, wherein the processor is configured to perform control to highlight the extracted region.

6. The document creation support apparatus according to claim 1, wherein the processor is configured to perform control to display the generated comment on findings.

7. The document creation support apparatus according to claim 1, wherein the processor is configured to generate a plurality of comments on findings for one disease name.

8. The document creation support apparatus according to claim 7, wherein the processor is configured to:

perform control to display the plurality of generated comments on findings; and receive a comment on findings selected by a user.

9. The document creation support apparatus according to claim 7, wherein the processor is configured to:

estimate a disease name using the medical image; and control a display mode of the plurality of generated comments on findings based on an estimation result.

10. The document creation support apparatus according to claim 9, wherein the processor is configured to estimate the disease name based on a degree of similarity between the medical image and an image prepared in advance for each disease.

11. The document creation support apparatus according to claim 9, wherein the processor is configured to estimate the disease name based on a statistical value of pixel values in the region extracted from the medical image.

12. The document creation support apparatus according to claim 9, wherein the processor is configured to estimate the disease name based on the medical image and a trained model that has been trained in advance using training data including a medical image for learning and a disease name of a disease included in the medical image for learning.

13. The document creation support apparatus according to claim 1, wherein the processor is configured to generate a plurality of comments on findings using a plurality of disease names.

14. The document creation support apparatus according to claim 1, wherein the processor is configured to perform control to display, in an identifiable manner, a status for the extracted region among a plurality of statuses related to creation work of a medical document by a user.

15. The document creation support apparatus according to claim 14, wherein the plurality of statuses include two or more of a status in which the user has not confirmed the region, a status in which the user has designated the region as a target of the creation work and the creation work is incomplete, a status in which the user has designated that the region is excluded from the target of the creation work, and a status that the creation work for the region is completed.

16. The document creation support apparatus according to claim 15, wherein the processor is configured to,
in a case where the status is the status in which the user has designated the region as the target of the creation work and the creation work is incomplete, perform control to display the status in an identifiable manner by adding a predetermined mark to the region.

17. The document creation support apparatus according to claim 14, wherein the processor is configured to
further perform control to display a list of information regarding each of a plurality of the regions.

18. The document creation support apparatus according to claim 17, wherein the processor is configured to
perform control to display the list of the information regarding each of the plurality of regions for each of the statuses.

19. A document creation support method executed by a processor provided in a document creation support apparatus, the method comprising:

extracting regions having one or more preset physical features from a medical image according to a brightness condition of each of the regions, wherein a pixel value of each of the regions is within a set range;

performing control to display information indicating the extracted region, wherein the information indicating the extracted region comprises at least information indicating under which brightness condition each of the plurality of regions is extracted;

receiving information indicating a selected region from among the extracted regions;

accessing a memory to refer to a disease name table in which the physical features and disease names are associated with each other; and generating a comment on findings using a disease name associated with a physical feature of the selected region.

20. A non-transitory computer-readable storage medium storing a document creation support program for causing a processor provided in a document creation support apparatus to execute:

extracting regions having one or more preset physical features from a medical image according to a brightness condition of each of the regions, wherein a pixel value of each of the regions is within a set range;

performing control to display information indicating the extracted region, wherein the information indicating the extracted region comprises at least information indicating under which brightness condition each of the plurality of regions is extracted;

receiving information indicating a selected region from among the extracted regions;

accessing a memory to refer to a disease name table in which the physical features and disease names are associated with each other; and generating a comment on findings using a disease name associated with a physical feature of the selected region.

\* \* \* \* \*